United States Patent
Pellegrino et al.

(10) Patent No.: US 7,372,940 B2
(45) Date of Patent: May 13, 2008

(54) RADIATION THERAPY SYSTEM WITH RISK MITIGATION

(75) Inventors: Anthony J. Pellegrino, New Fairfield, CT (US); Francis P. Carrasco, Danbury, CT (US)

(73) Assignee: Topel, LLC, Danbury, CT (US)

( * ) Notice: Subject to any disclaimer, the term of this patent is extended or adjusted under 35 U.S.C. 154(b) by 0 days.

(21) Appl. No.: 11/356,455

(22) Filed: Feb. 15, 2006

(65) Prior Publication Data

US 2007/0076847 A1    Apr. 5, 2007

Related U.S. Application Data

(63) Continuation-in-part of application No. 11/240,919, filed on Sep. 30, 2005.

(51) Int. Cl.
*A61N 5/10* (2006.01)

(52) U.S. Cl. .......................... 378/65; 378/97

(58) Field of Classification Search ................. 378/65, 378/96, 97, 108, 163, 165, 210, 63, 117; 600/427–429
See application file for complete search history.

(56) References Cited

U.S. PATENT DOCUMENTS

| | | | |
|---|---|---|---|
| 2,506,342 A | 5/1950 | Burke | |
| 3,999,073 A | 12/1976 | Hounsfield | |
| 4,063,099 A * | 12/1977 | Grassme | 378/39 |
| 4,277,685 A | 7/1981 | Covic | |
| 4,386,863 A * | 6/1983 | Rooney | 400/185 |
| 4,528,685 A | 7/1985 | Kump et al. | |
| 4,649,558 A * | 3/1987 | Brunn et al. | 378/97 |
| 4,894,855 A | 1/1990 | Kresse | |
| 5,081,660 A | 1/1992 | Fujisaki | |
| 5,755,519 A * | 5/1998 | Klinefelter | 400/249 |
| 5,835,555 A | 11/1998 | Barry | |
| 6,241,670 B1 * | 6/2001 | Nambu | 600/427 |
| 6,325,537 B1 | 12/2001 | Watanabe | |
| 6,421,416 B1 * | 7/2002 | Sliski et al. | 378/65 |
| 6,453,262 B1 * | 9/2002 | Kitamura | 702/145 |
| 2003/0048875 A1 | 3/2003 | Mihara | |
| 2004/0260142 A1 * | 12/2004 | Lovoi | 600/1 |
| 2005/0078792 A1 * | 4/2005 | Strommer | 378/96 |

OTHER PUBLICATIONS

"Therapax 150 Microprocessor-Controlled Superficial Radiation Treatment System" brochure by Pantak, Inc., 1996.
"D3150 Superficial X-Ray Therapy System" by Gulmay Medical, Document No. GM-1508-1, Issue Date: Nov. 2000.
"RT-100 Superficial and Endotherapy Apparatus" Product Data issued by N.V. Phillips' Glaelampenfabricken, Medical Systems divsision, Eindhoven Netherlands, Supercedes Product ..continued . . . Data XK1025 dated X-'69.

* cited by examiner

*Primary Examiner*—Edward J. Glick
*Assistant Examiner*—Anastasia S. Midkiff
(74) *Attorney, Agent, or Firm*—Ware, Fressola, Van Der Sluys & Adolphson, LLP

(57) ABSTRACT

An X-ray therapy system with equipment for reducing risk that the radiation applied to a patient is other than what is intended. A radiation check is made in which a signal indicative of the radiation to be applied is compared with a reference signal, and/or a configuration check is made using sensors to automatically sense the applicator being used to apply the radiation to the patient.

11 Claims, 7 Drawing Sheets

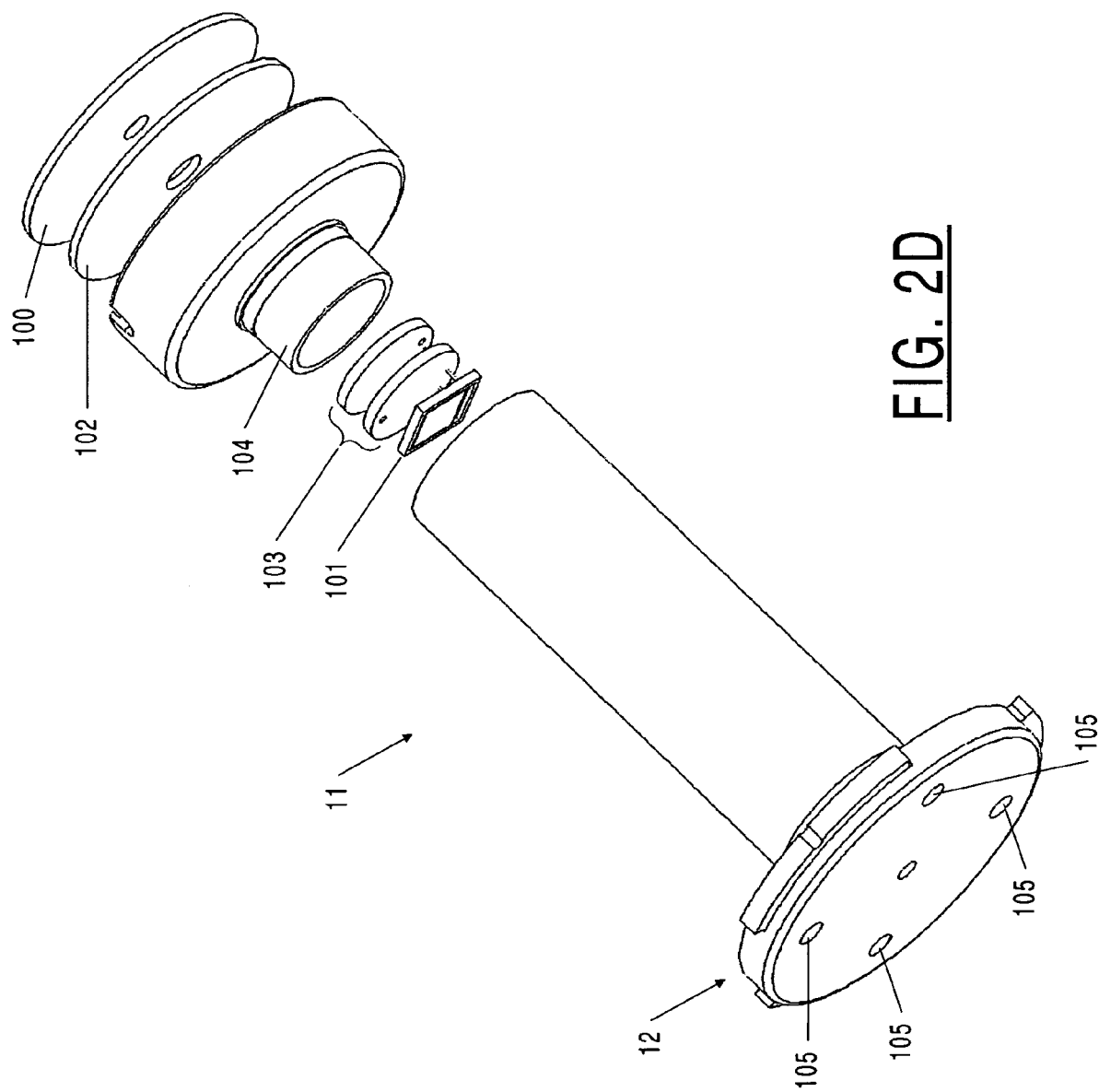

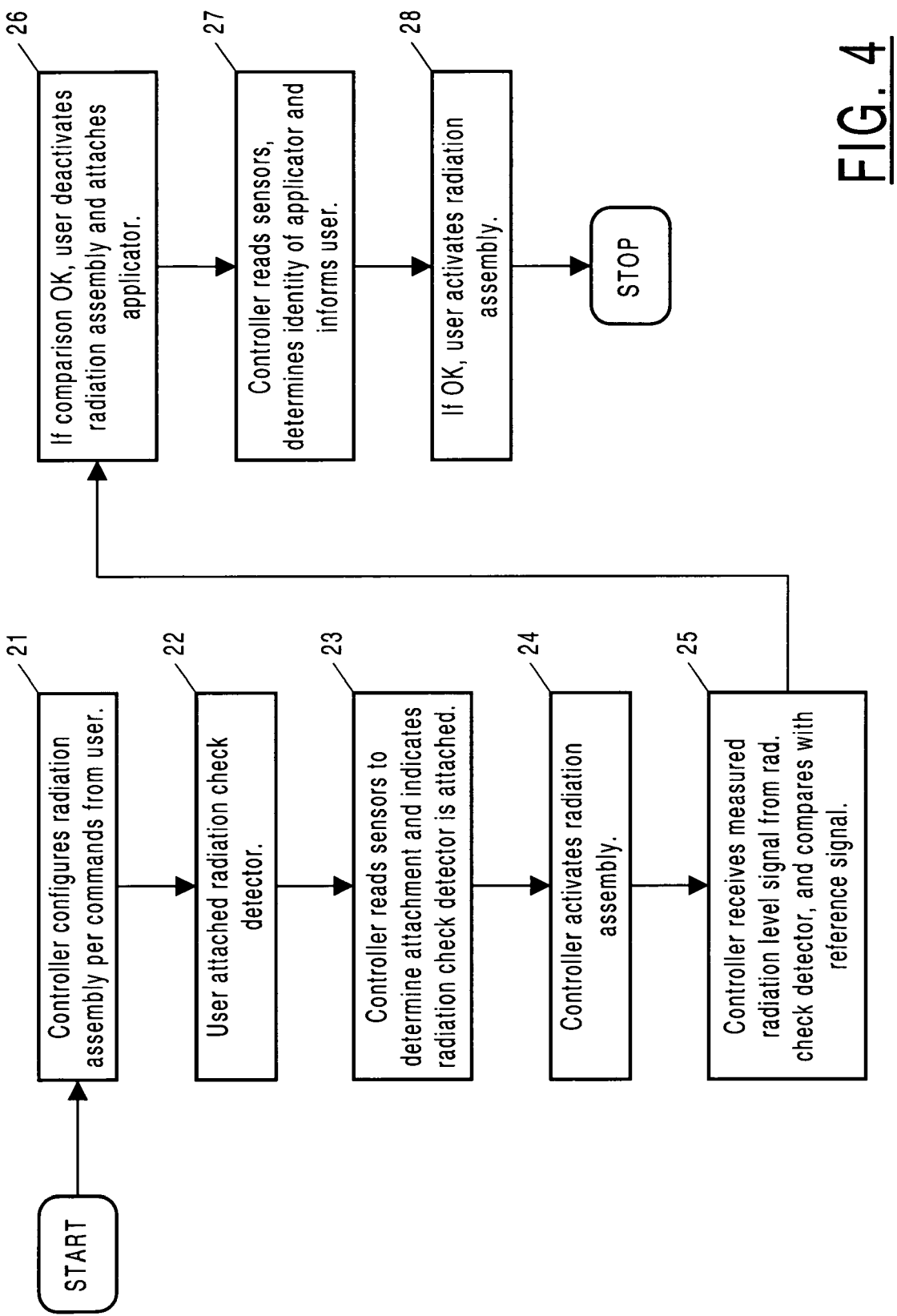

RADIATION THERAPY SYSTEM WITH RISK MITIGATION

CROSS REFERENCE TO RELATED APPLICATIONS

This application is a continuation-in-part of U.S. patent application Ser. No. 11/240,919 filed Sep. 30, 2005, from which priority is claimed under all applicable sections of Title 35 of the United States Code.

BACKGROUND OF THE INVENTION

1. Technical Field

The present invention relates to a radiation system for treating patients with certain skin conditions, such as skin cancer; and more particularly, it relates to a low energy or superficial x-ray radiation therapy system equipped with x-ray filters for regulating the characteristics of the radiation.

2. Discussion of Related Art

So-called superficial x-rays are low energy x-rays useful for treating certain disease conditions occurring typically just below the skin, conditions such as skin cancers and dermatological disorders. A superficial radiation therapy system includes an X-ray tube and a filter so as to deliver most of the radiation at or just below the skin surface. In superficial radiation therapy treatment, an X-ray dose is provided to a patient by providing X-rays at a desired energy and at a desired intensity for a desired time, and by situating the patient at a desired distance from the X-ray tube. Commercially available superficial x-ray therapy systems, such as PHILIPS RT.-100, THERAPAX 150 and GULMAY D3150, have a radiation assembly with several adjustable voltages (in kilovolts), i.e. the voltage between the cathode and the anode of the X-ray tube, and corresponding current (in milliamps). For example the PHILIPS RT-100 has settings of 10/8, 20/10, 30/10, 37/10, 45/10, 55/10 70/10, 85/8, and 100/8 kV/mA. The skin area of the patient to receive the X-ray dose is typically situated a distance of from 10 cm to 25 cm from a focal spot within the X-ray tube. The skin area is positioned relative to the X-ray tube using what is called an applicator, which attaches to a housing for the X-ray tube.

A control panel is used to indicate the desired X-ray energy and intensity level, based on a periodic calibration of the radiation therapy system usually performed from time to time by a health physicist.

In providing an X-ray dose to a patient, as mentioned above a filter is normally used. It is often made with a metal such as copper or aluminum. Some low energy radiation is absorbed in the filter plate, and the radiation passing through the filter has a narrower spectrum. In existing superficial radiation treatment systems such as PHILIPS RT-100, there are as many as nine filters in varying materials and thickness, each is used for one particular voltage/current setting of the x-ray tube. A user (i.e. an operator of the X-ray therapy system) sets up a filter according to the X-ray tube setting by inserting a filter plate. An incorrect insertion of a filter can result in improper radiation level—i.e. a rate of irradiation, in e.g. roentgens per unit time—and also radiation that is shifted in its average energy, and so can lead to an improper dose being delivered to the patient.

The radiation dose provided by the X-ray tube can also vary from what is intended even if the filtering is as intended and even if the last calibration was performed correctly, because the characteristics of the X-ray tube can change over time due to normal wear and tear, and due to environmental factors (e.g. temperature cycling or changes), or the X-ray tube can simply malfunction.

The actual delivered radiation level should typically be within about 5% of the intended radiation level (in e.g. roentgens per unit time), and if it is determined that the actual radiation level differs by more than about 5%, the radiation therapy system must usually be serviced because such a difference can cause the therapy to be either ineffective (if the level is too low by more than 5%) or even unnecessarily harmful (if the level is too high).

What is needed is a simple way to check the radiation level before treating a patient. Since the radiation level depends on the radiation level provided by the radiation assembly (including any filtering) and also the applicator being used, the radiation level should be checked, and the applicator identity should be confirmed.

DISCLOSURE OF INVENTION

Accordingly, in a first aspect of the invention, a radiation therapy system is provided, comprising: a radiation assembly, responsive to a control signal indicating a desired radiation level, for providing radiation having an actual radiation level; an applicator attachment, mechanically coupled to the radiation assembly, for receiving the radiation and for applying the radiation to a location of a patient as an actual applied radiation level; and means for reducing the risk that the actual applied radiation level differs from an intended applied radiation level.

In accord with the first aspect of the invention, the means for reducing risk may comprise: a radiation check detector, including a detector at a distal end of a housing structure and having a coupler at a proximal end for mechanically coupling the housing structure to the radiation assembly and for orienting the radiation check detector relative to the radiation assembly so as to expose the detector to the radiation at a desired distance from the radiation assembly, the radiation check detector for providing a detector signal corresponding to the actual radiation level; and a controller, for providing the control signal indicating the desired radiation level, and responsive to the detector signal corresponding to the actual radiation level, for comparing the detector signal to a reference signal, and for providing a warning signal if the comparison finds a difference by more than a predetermined amount.

Also in accord with the first aspect of the invention, the means for reducing risk may comprise: one or more sensors in the radiation assembly at different locations proximate to where the attachment couples to the radiation assembly, and wherein each sensor provides a signal indicative or whether a magnet is sensed; one or more magnets in the attachment positioned at locations corresponding to the locations of at least some of the sensors; and means for determining from the sensor signals in combination whether the attachment is coupled to the radiation assembly or whether another or if any attachment is so coupled.

A corresponding method is also provided, in a second aspect of the invention.

BRIEF DESCRIPTION OF THE DRAWINGS

The above and other objects, features and advantages of the invention will become apparent from a consideration of the subsequent detailed description presented in connection with accompanying drawings, in which:

FIG. 2D is an exploded view of a radiation check detector, showing embedded in the end that attaches to the coupler of the radiation assembly four magnets, at locations corresponding to the locations of the sensors shown in FIG. 3.

FIG. 3B also shows a magnet on the applicator, positioned so as to be sensed by one of the Hall effect switches.

FIG. 4 is a flowchart illustrating operation of a radiation therapy system according to the invention.

BEST MODE FOR CARRYING OUT THE INVENTION

The invention reduces risk in providing X-ray radiation therapy.

Figure 1:
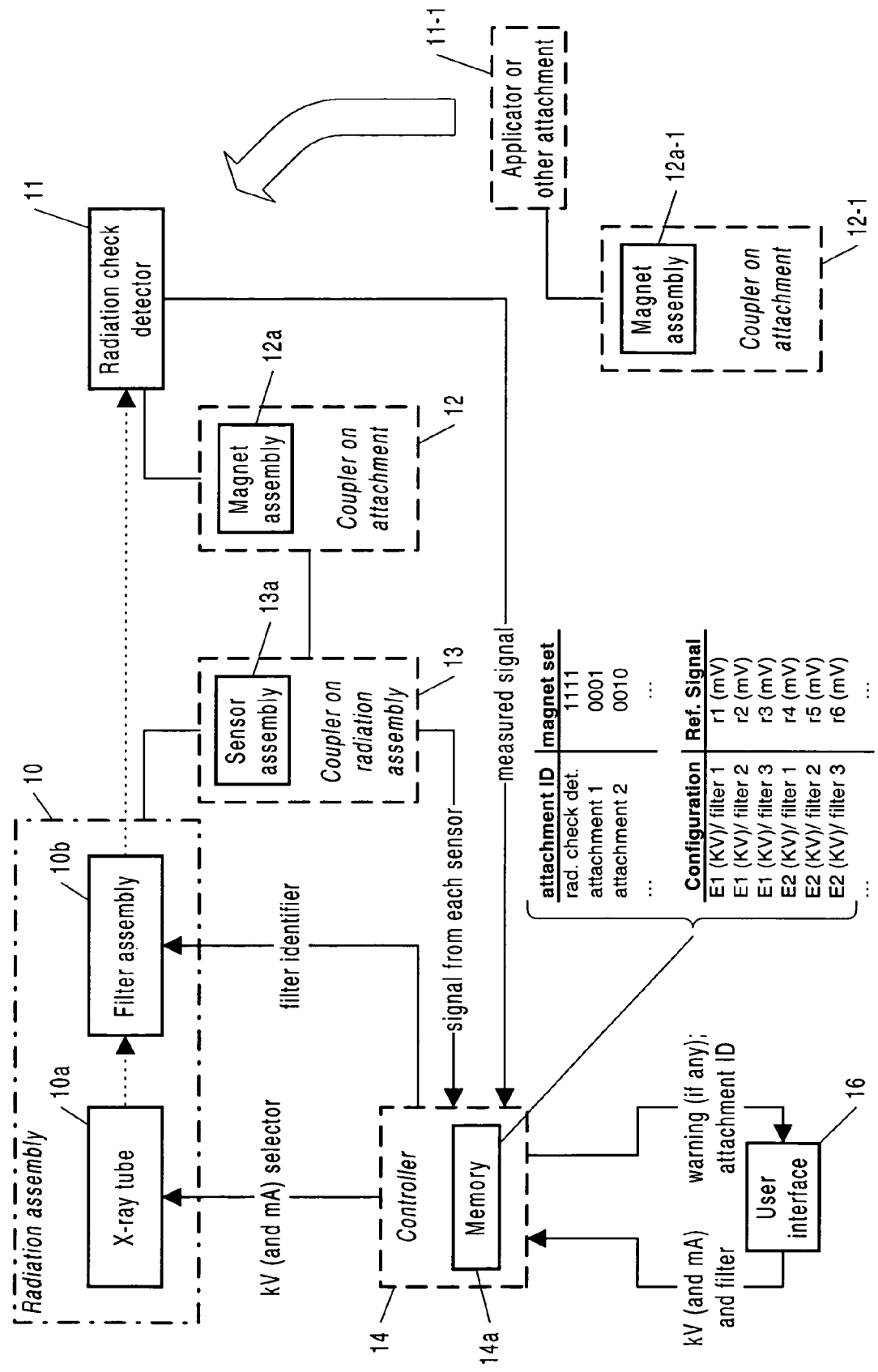
FIG. 1 is a block diagram/flow diagram of a radiation therapy system according to the invention, including a radiation assembly for providing filtered X-ray radiation, and an applicator for applying the radiation to a location on the skin of a patient, and also indicating a radiation check detector as one component used in risk mitigation.

Referring to FIG. 1, a radiation therapy system, as that term is used here, indicates a system that provides X-ray irradiation using a radiation assembly 10 including an X-ray tube 10a and usually a filter of a filter assembly 10b. Such a system includes one or another applicator 11-1 mechanically coupled to the radiation assembly at a coupling location via a coupler 12 on the applicator and a coupler 13 on the radiation assembly, to apply the radiation to a spot usually just beneath the skin of a patient. The radiation applied to the spot is applied at what is here called a radiation level, i.e. an amount of X-ray radiation per unit time, such as roentgens per minute. (A roentgen is a unit of exposure of X-ray or gamma ray radiation, which is ionizing radiation; it is the amount of radiation required to liberate positive and negative charges of one electrostatic unit of charge in 1 cm$^3$ of air at standard temperature and pressure.)

The insertion of a particular filter is typically done automatically, i.e. a filter is selected by the operator via a user interface 16 to a controller 14, and the controller sends a control signal to a motor (not shown) of the filter assembly causing the motor to position the selected filter between the X-ray tube and the applicator coupling location.

The invention allows an operator of a radiation therapy system to ensure that the (X-ray) radiation level intended for a patient is in fact the intended level, preliminary to treating the patient. The delivered radiation level depends on the radiation assembly providing an expected level of radiation (in e.g. roentgens per min) and also depends on the particular applicator (each of which provides a possibly different source-to-skin distance or exposes a different sized area of the patient's skin to the radiation).

Thus, there are two aspects to ensuring that the radiation level is correct: the radiation level from the X-ray tube as filtered should be checked, and the configuration of the radiation therapy system just prior to treatment should then be confirmed, i.e. the applicator or other attachment coupled/attached to the radiation assembly should be identified.

According to the invention, in preparation for treating a patient, an operator inputs to the controller 14 the radiation assembly configuration (the voltage/current, and also the filter). The selection of the filter causes the motor (not shown) of the filter assembly 10b to move (in fact typically rotate) the selected filter in place so that it is situated between the radiation assembly and the location of coupling to an attachment (e.g. an applicator). Next, an applicator 11-1 is selected, which can mechanically couple to the radiation assembly via its coupler 12-1. However, instead of coupling the applicator, the operator mechanically couples/ attaches a radiation check detector 11 to the radiation assembly. The radiation check detector uses preferably a rapid radiation level assessment technology, such as photodiodes, to detect the X-rays. The radiation assembly is then turned on, and the radiation check detector provides a signal (typically a voltage) corresponding to the radiation it detects, indicating a radiation level (i.e. corresponding to e.g. roentgens per min.). The signal from the radiation check detector is provided to the controller, which compares the signal with a reference signal for the selected radiation assembly configuration (the voltage/current and filter combination input by the operator). (The reference signal used may also depend on the radiation check detector, in case there are different radiation check detectors having different characteristics, in which case the controller finds the reference signal for the particular radiation check detector in use.) If the comparison finds a difference of more than some predetermined amount (e.g. 5%), the controller issues a warning via a user interface, so that the operator knows that the radiation therapy system is not providing radiation at the intended/expected level, and the radiation therapy system (or at least the X-ray tube component) must be serviced.

In actual practice, the radiation therapy system is periodically calibrated (e.g. a few times each year) using e.g. an ionization chamber or other technology able to provide an absolute measurement (as opposed to a relative measurement), to establish an actual radiation level at some reference location, for each possible configuration of the radiation assembly, i.e. for each voltage/current-filter combination. Assuming that the measurement determines that the actual radiation level is useable, the measured absolute radiation level is then stored in the controller so as to be associated with the voltage/current and filter used during the calibration/measurement, and a radiation check detector is then (more or less immediately thereafter) coupled to the radiation assembly, and the signal (typically some voltage) output by the radiation check detector when exposed to the radiation using the same voltage/current-filter configuration is then recorded as the reference (for the configuration in use). This reference signal then corresponds to the measured absolute value (for the configuration in use). (Instead of simply measuring the radiation level, the radiation assembly may be adjusted or serviced, of course, with the result that the output changes to a desired level, and the adjusted actual output is then used as the measured actual value.)

Following the radiation check, assuming that the check does not produce a warning signal, the applicator selected for the treatment is attached. Then, also in accord with the invention, the controller indicates to the operator of the radiation therapy system, which (if any) of the applicators is attached via its mechanical coupling 12-1 for coupling to the radiation assembly, or if instead the radiation check detector 11 is attached/coupled to the radiation assembly via its coupler 12. According to the invention, the controller provides this indication based on signals from sensors (such as Hall effect sensors/switches) of a sensor assembly 13*a* embedded in the coupler 13 on the radiation assembly. The sensors respond to magnets (such as samarium cobalt magnets) in a magnet assembly 12*a* located at various positions—such as any one or more of four different positions—in the coupler 12 of the radiation check detector 11 and the coupler 12-1 of each applicator 11-1. Different combinations of magnets are used in the different attachments; e.g. one applicator can have a magnet at a first location, no magnet at a second, and a magnet at a third location and also a fourth. The output of all the sensors (from polling/interrogating/reading the individual sensors) then allows the controller 14 to determine which combination of magnets (if any) is present, and so which attachment is coupled to the radiation assembly 10. (Each sensor simply indicates whether it senses a magnet.) The controller typically uses a table stored in memory accessible to the controller and indicating which set of sensors should signal for each different possible attachment.

For example, the sensor assembly 13*a* could include four sensors positioned at different locations in the coupler 13 on the radiation assembly, and from one to four magnets could be placed in an attachment at corresponding locations (so as to be able to be sensed by the sensor at the corresponding location in the radiation therapy frame) in the coupler 12 or 12-1 for the attachment (the radiation check detector 11 or the applicator 11-1). In such an embodiment, the controller could distinguish up to 15 different possible attachments, and also indicate that no attachment is present.

Figure 2A:
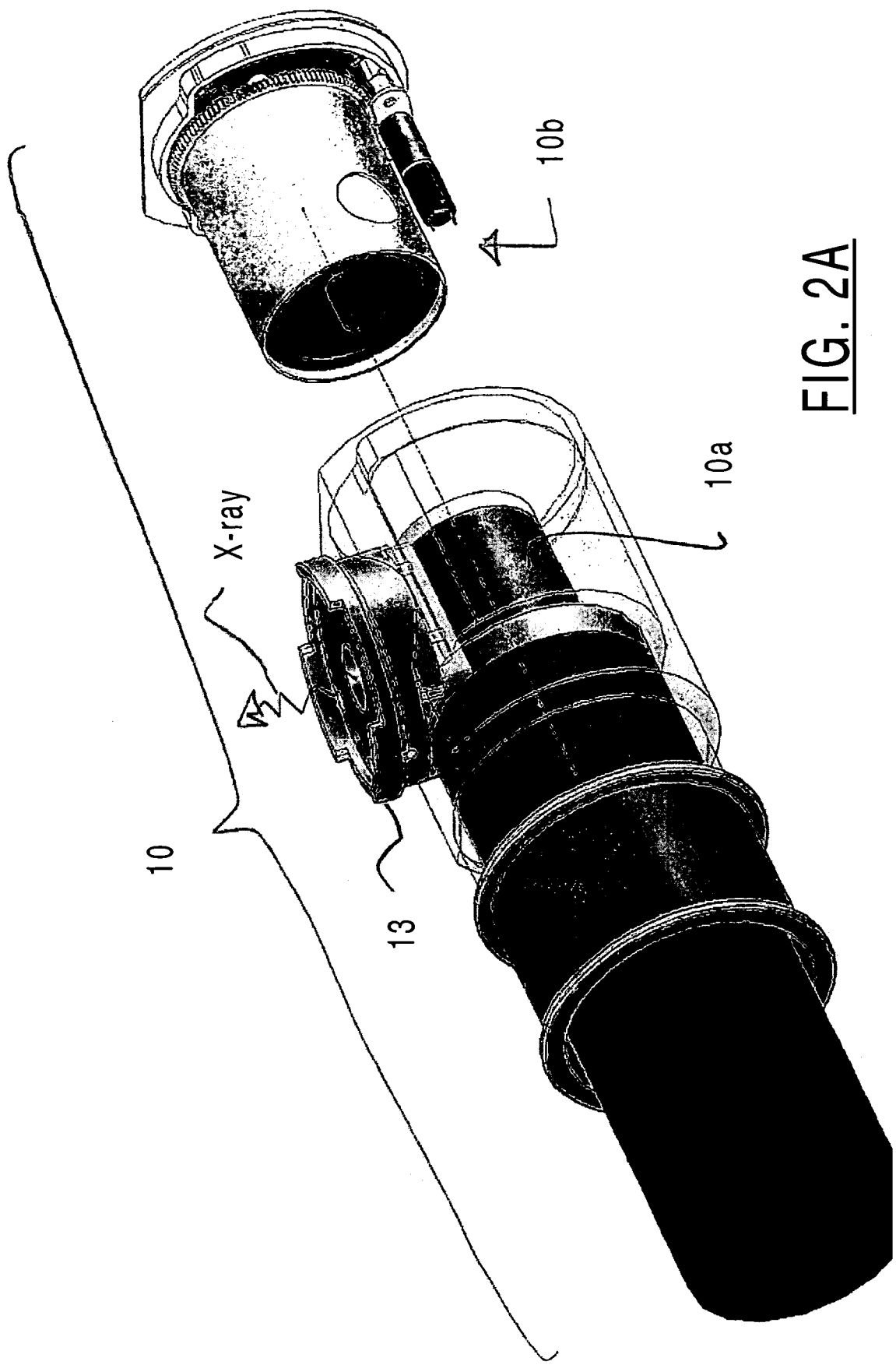
FIGS. 2A and 2B are partial exploded perspective views of a radiation assembly according to the invention.
Figure 2B:
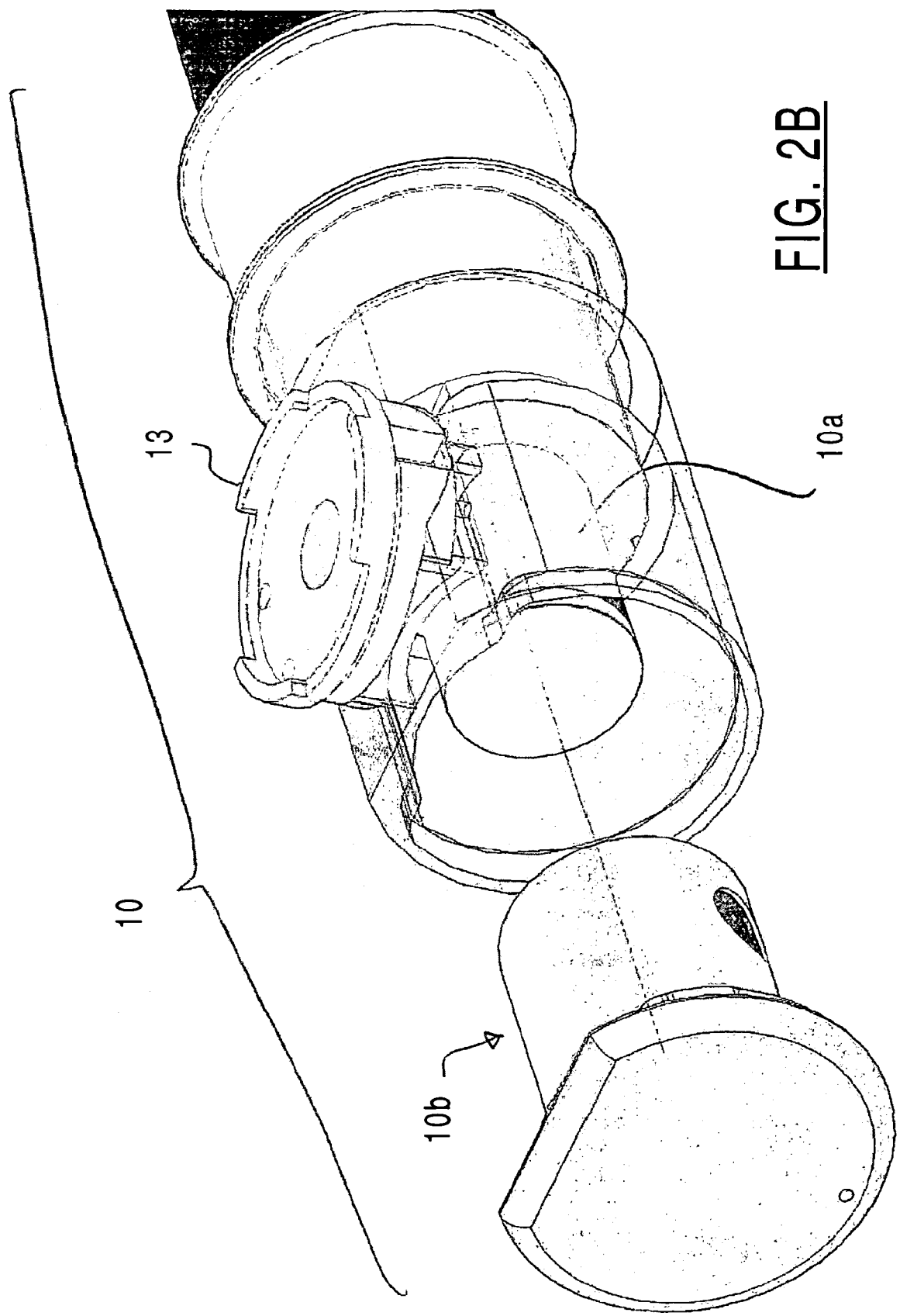

FIGS. 2A and 2B show partial exploded perspective views of the basic components of the radiation assembly 10 (FIG. 1), which includes an X-ray tube 10*a* arranged in relation to a filter assembly generally indicated as 10*b*. The filter assembly 10*b* includes is a rotatable mechanism; it is positioned over the X-ray tube and rotated (via control signals to a drive unit) so as to place one or another filter between the X-ray tube and the location where an applicator or radiation check detector is attached/coupled to the radiation assembly.

Figure 2C:
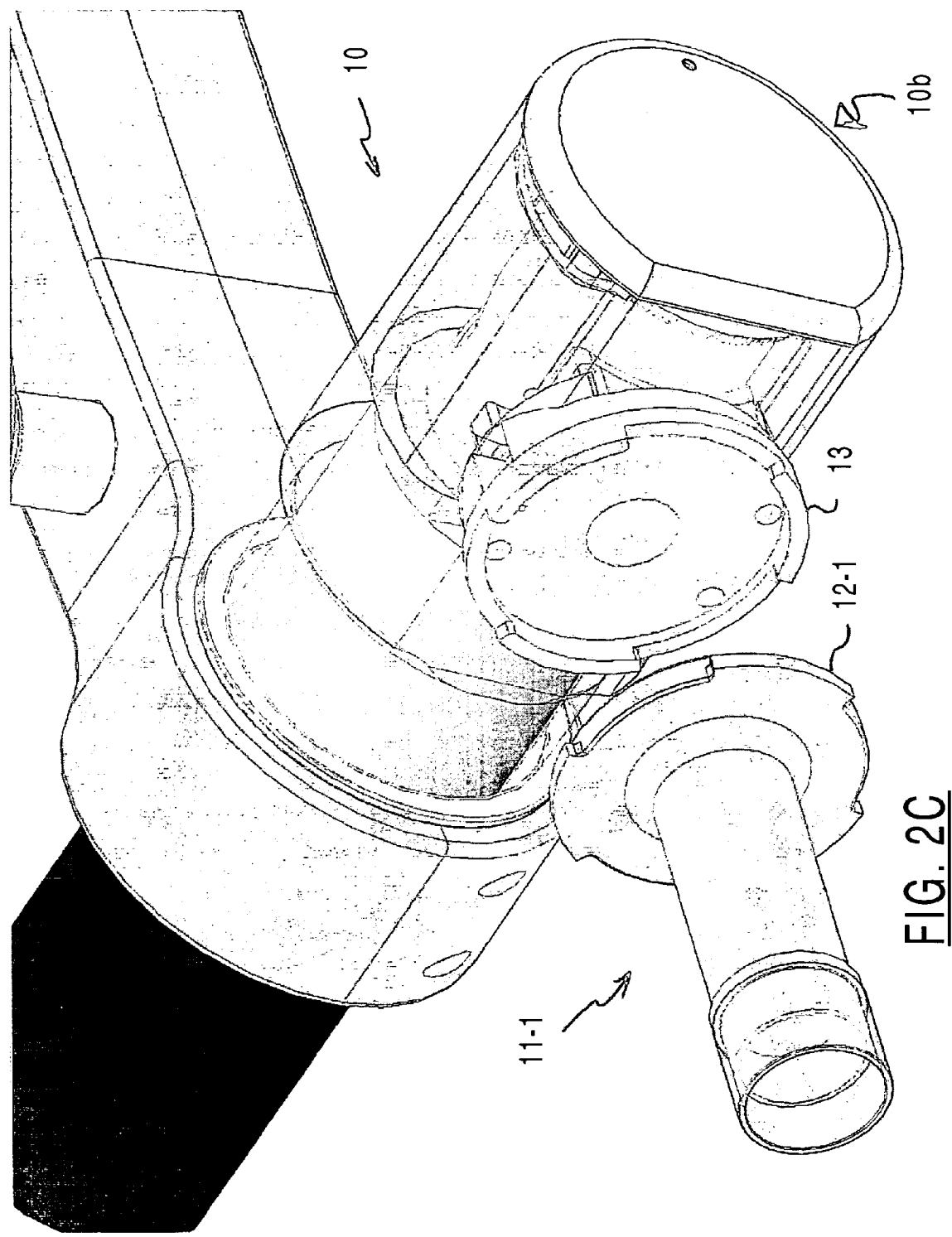
FIG. 2C shows a perspective exploded view of an applicator arranged in relation to the radiation assembly.

FIG. 2C shows the applicator 11-1 having a coupler 12-1 for coupling to the corresponding coupler 13 of the radiation assembly.

FIG. 2D is an exploded view of the detector 11 having a coupler 12 for coupling to the corresponding coupler 13 of the radiation assembly. The detector includes a photodiode 101 connected to a printed circuit board and amplifier 102 via electrical wires that pass through offset holes in two lead discs 103. The detector includes shielding 104 that surrounds the photodiode, and an endplate 100 behind the printed circuit board and amplifier. In addition, four magnets 105 of the magnet assembly 12*a* on the coupler 12 are shown.

Figure 3B:
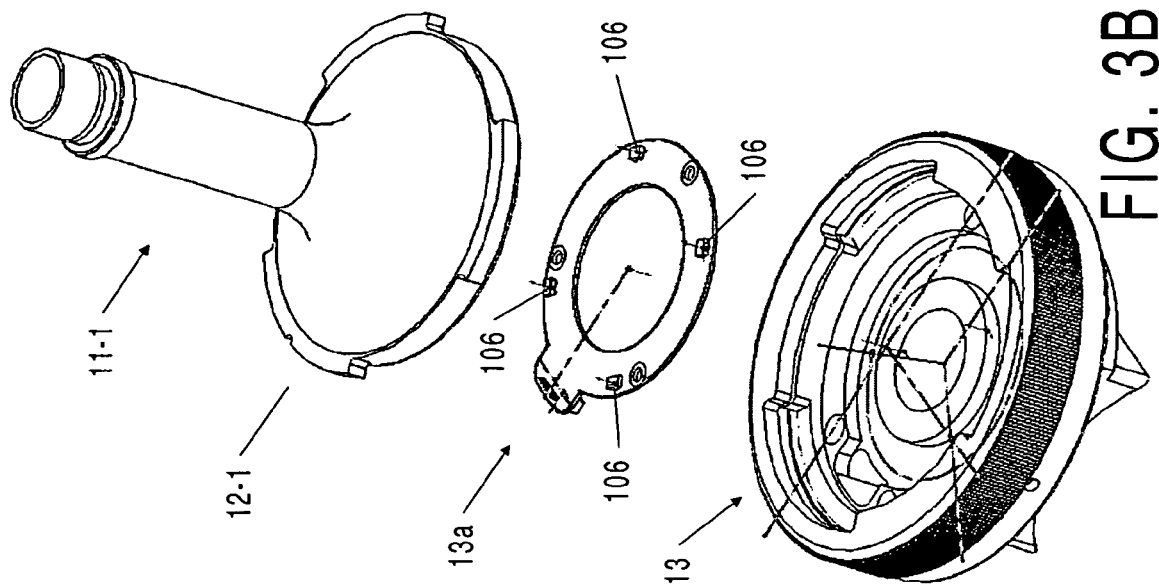
FIGS. 3A and 3B each show a different perspective exploded view of an applicator and the coupler on the radiation assembly to which the applicator attaches, and also show hall-effect switches in the coupler, serving as another component providing risk mitigation according to the invention.
Figure 3A:
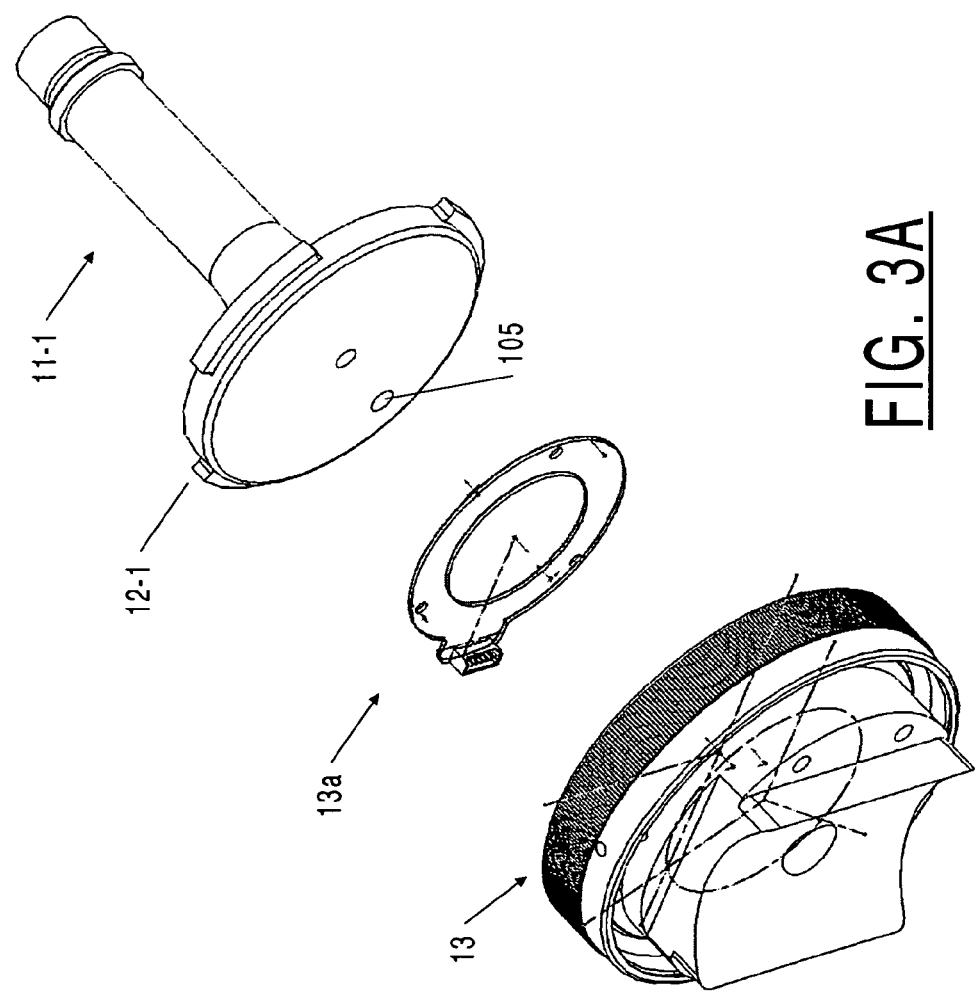

FIGS. 3A and 3B show the coupler 13 on the radiation assembly and shows (in exploded view) the sensor assembly 13*a*, including four Hall effect switches 106 at locations suitable for sensing the magnets 105 in the coupler 12 of the radiation check detector 11, or for checking for the presence of the (single) magnet 105 in the applicator 11-1, also shown. The sensor assembly is typically potted and then positioned in the coupler 13. The applicator 11-1 is also shown, but the magnet(s) in the coupler 12-1 are not visible in FIG. 3A, but are visible in FIG. 3B.

Thus, and now referring to FIGS. 1-3 and also to FIG. 4, in a first step 21 in the operation of the radiation therapy system of FIG. 1, a user inputs via the user interface 16 an indication of the voltage/current to be used, and also the filter and the controller configures the radiation assembly accordingly. In a next step 22, the user attaches the radiation check detector 11 to the radiation assembly, and in a next step 23, the controller reads the sensors of the sensor assembly 13*a* and indicates to the identifier for the attachment, by referring to the table of attachment identifiers vs. magnet sets (see FIG. 1) held in the memory 14*a* in the controller. (For example, the magnet set for the radiation check detector might be all four magnets, i.e. magnet number 1, 2, 3 and 4, which would be indicated in the table using code 1111, whereas magnet set having only magnet number 2 would be indicated in the table using code 0010.) Assuming the radiation check detector is indicated as attached, in a next step 24, in response to user commands, the controller activates the radiation assembly. In a next step 25, the controller receives a signal from the radiation check detector (indicative of the radiation level detected by the check detector), and compares the signal with the reference signal in its memory 14*a*, using the table of configuration vs. reference signals to find the appropriate reference signal. If the comparison finds a difference by less than a predetermined amount, the controller so indicates, but issues a warning otherwise. Assuming the comparison finds a negligible difference, then in a next step 26 the user attaches the applicator 11-1 in place of the radiation check detector, and in a next step 27, the controller identifies the attachment as the applicator, and in a final step 28, after the patient is properly positioned, the user activates the radiation assembly so begin the radiation therapy.

As shown in FIG. 1, the memory 14*a* includes a reference signal for each possible kV/filter combination. It also includes the actual absolute value for the combination, as determined by the periodic calibration. (The absolute value is not indicated in FIG. 1.)

The invention must therefore be understood as providing a way to reduce risk in providing radiation therapy, the risk that the actual applied radiation is other than what is intended. The risk is reduced, in one aspect of the invention, by checking the radiation level using the radiation check detector. In another aspect of the invention, the risk is reduced by checking that the intended attachment (one or another of the applicators or the radiation check detector) is attached (the checking here being based on reading the sensors attached to the radiation assembly).

It is to be understood that the above-described arrangements are only illustrative of the application of the principles of the present invention. Numerous modifications and alternative arrangements may be devised by those skilled in the art without departing from the scope of the present invention, and the appended claims are intended to cover such modifications and arrangements.

What is claimed is:

1. A radiation therapy system, comprising:
 a radiation assembly, responsive to a control signal indicating a desired radiation level, for providing radiation having an actual radiation level;
 an applicator attachment, mechanically coupled to the radiation assembly, for receiving the radiation and for applying the radiation as an actual applied radiation level to a predetermined location where a target site of a patient is positioned; and
 means for reducing the risk that the actual applied radiation level differs from an intended applied radiation level, including means for measuring the radiation level at the predetermined location and for automatically comparing the measured radiation level with the intended radiation level.

2. A radiation therapy system as in claim 1, wherein the means for reducing risk comprises:
- a radiation check detector, including a detector at a distal end of a housing structure and having a coupler at a proximal end for mechanically coupling the housing structure to the radiation assembly and for orienting the radiation check detector relative to the radiation assembly so as to locate the detector at the predetermined location, the radiation check detector for providing a detector signal corresponding to the actual radiation level; and
- a controller, for providing the control signal indicating the desired radiation level, and responsive to the detector signal corresponding to the actual radiation level, for comparing the detector signal to a reference signal, and for providing a warning signal if the comparison finds a difference by more than a predetermined amount.

3. A radiation therapy system as in claim 2, wherein the mechanical coupling by which the radiation check detector couples to the radiation assembly is the same as a mechanical coupling by which an applicator used for delivering radiation to a patient couples to the radiation assembly.

4. A radiation therapy system as in claim 2, wherein the radiation check detector housing includes a magnet at a location on the proximal end, and wherein the radiation therapy system further comprises a sensor for providing a signal if the magnet is sensed, thereby providing an indication of whether the radiation check detector is coupled to the radiation assembly.

5. A radiation therapy system as in claim 4, wherein the radiation therapy system further comprises other sensors, and the radiation therapy system includes a coupler mechanism for mating with the coupler of either the radiation check detector or one or another applicator, and wherein the radiation check detector and the one or another applicator each has one or more magnets at locations corresponding to the locations of the sensors, and wherein each sensor provides a signal indicative or whether a magnet is sensed, and the radiation therapy system uses the signals in combination to determine which if any of the applicators or the radiation check detector is coupled to the radiation assembly.

6. A radiation therapy system as in claim 1, wherein the means for reducing risk further comprises:
- one or more sensors in the radiation assembly at different locations proximate to where the attachment couples to the radiation assembly, and wherein each sensor provides a signal indicative of whether a magnet is sensed;
- one or more magnets in the attachment each positioned at a different location corresponding to one of the different locations of the one or more sensors; and
- means for determining from the sensor signals in combination whether the attachment is coupled to the radiation assembly or whether another or if any attachment is so coupled.

7. A method of operation of a radiation therapy system, comprising:
- a step of using a radiation assembly to provide radiation having an actual radiation level;
- a step of using an applicator attachment, mechanically coupled to the radiation assembly, to receive the radiation and to apply the radiation as an actual applied radiation level to a predetermined location where a target site of a patient is positioned; and
- a step of reducing the risk that the actual applied radiation level differs from an intended applied radiation level, including measuring the radiation level at the predetermined location and automatically comparing the measured radiation level with the intended radiation level.

8. A method as in claim 7, wherein the step of reducing risk comprises:
- a step of using a radiation check detector mechanically coupled to the radiation assembly to provide a detector signal indicative of the actual radiation level at the predetermined location; and
- a step of comparing the detector signal to a reference signal and providing a warning signal if the comparison finds a difference by more than a predetermined amount.

9. A method as in claim 8, wherein the radiation check detector housing includes a magnet at a location on the proximal end, and wherein the method further comprises using a sensor in or attached to the radiation assembly to provide a signal if the magnet is sensed, thereby providing an indication of whether the radiation check detector is coupled to the radiation assembly.

10. A method as in claim 9, wherein the method further comprises also using other sensors in or attached to the radiation assembly, wherein the radiation assembly can be coupled to either the radiation check detector or one or another applicator, and wherein the radiation check detector and the one or another applicator each includes one or more magnets at locations corresponding to the locations of the sensors when coupled to the radiation assembly, and wherein the method further comprises using each sensor to provide a signal when it senses a magnet and using the signals in combination to determine which if any of the applicators or the radiation check detector is coupled to the radiation assembly.

11. A method as in claim 7, wherein the step of reducing risk further comprises:
- a step of using a plurality of sensors at different locations in the radiation assembly all proximate to where the attachment couples to the radiation assembly, wherein each sensor provides a signal indicative of whether a magnet is sensed;
- a step of including in the applicator attachment a magnet at each of at least some different locations each corresponding to a different one of the locations of the plurality of sensors; and
- a step of determining from the sensor signals in combination whether the applicator attachment is coupled to the radiation assembly or whether another or if any attachment is so coupled.

* * * * *